(12) United States Patent
Stergiopulos et al.

(10) Patent No.: US 11,779,489 B2
(45) Date of Patent: Oct. 10, 2023

(54) APPARATUS FOR TREATING EXCESS INTRAOCULAR FLUID HAVING AN ELASTIC MEMBRANE

(71) Applicant: Ecole Polytechnique Federale De Lausanne (EPFL), Lausanne (CH)

(72) Inventors: Nikolaos Stergiopulos, Preverenges (CH); Constantinos Stergiopulos, Lausanne (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 107 days.

(21) Appl. No.: 17/188,615

(22) Filed: Mar. 1, 2021

(65) Prior Publication Data
US 2021/0275356 A1    Sep. 9, 2021

Related U.S. Application Data

(60) Provisional application No. 62/986,604, filed on Mar. 6, 2020.

(51) Int. Cl.
*A61F 9/007* (2006.01)
(52) U.S. Cl.
CPC .................. *A61F 9/00781* (2013.01)
(58) Field of Classification Search
CPC .... A61F 9/007; A61F 9/0017; A61F 9/00781; A61F 2250/0013; A61M 27/002; F16K 17/00; F16K 17/02; F16K 99/0001; F16K 99/0015; F16K 99/0059; F16K 2099/008; F16K 2099/0084; F16K 99/0034; F16K 2099/0088; F16K 2099/0086;
(Continued)

(56) References Cited

U.S. PATENT DOCUMENTS

| 3,863,067 A | 1/1975 | Gooley |
| 4,232,451 A | 11/1980 | Thomsen |

(Continued)

FOREIGN PATENT DOCUMENTS

| EP | 1243826 A2 | 9/2002 |
| EP | 1484535 A1 | 12/2004 |

(Continued)

OTHER PUBLICATIONS

International Search & Written Opinion dated Sep. 14, 2017 in Int'l PCT Patent Appl. Serial No. PCT/IB2017/053294.

(Continued)

*Primary Examiner* — Jessica Arble
*Assistant Examiner* — Timothy L Flynn
(74) *Attorney, Agent, or Firm* — Eversheds Sutherland (US) LLP; Christopher C. Bolten; Albert K. Heng (57) ABSTRACT

Apparatus and methods are provided for treating diseases that produce elevated intraocular pressures, such as glaucoma, wherein the device includes a housing shell defining a cavity between a first end and a second end of the housing shell, and an elastic membrane disposed within the cavity to divide the cavity into a fluidic channel that permits a flow of fluid from the first end to the second end and a sealed cavity. The elastic membrane deforms to change the volume of the sealed cavity responsive to pressure fluctuations between the first and second ends, thereby varying the fluidic resistance of the flow of fluid through the fluidic channel.

21 Claims, 6 Drawing Sheets

(58) Field of Classification Search
CPC ............... F16K 2099/0094; G05D 16/00;
G05D 16/04; G05D 16/06; F04B 43/043;
F04B 39/1073; F04B 15/08; F04B
39/1066; F04B 43/04; Y10T 137/7891;
Y10T 137/7879; Y10T 137/7892; Y10T
137/7888
See application file for complete search history.

(56) References Cited

U.S. PATENT DOCUMENTS

| | | | |
|---|---|---|---|
| 4,457,757 A | 7/1984 | Molteno | |
| 4,585,005 A | 4/1986 | Lue et al. | |
| 4,856,972 A | 8/1989 | Van Benschoten et al. | |
| 4,950,232 A | 8/1990 | Ruzicka et al. | |
| 5,117,870 A | 6/1992 | Goodale et al. | |
| 5,300,020 A | 4/1994 | L'Esperance, Jr. | |
| 5,342,025 A | 8/1994 | Hwang | |
| 5,411,473 A | 5/1995 | Ahmed | |
| 5,454,840 A | 10/1995 | Krakovsky et al. | |
| 5,586,872 A | 12/1996 | Skobelev et al. | |
| 5,601,094 A | 2/1997 | Reiss | |
| 5,626,558 A | 5/1997 | Suson | |
| 5,938,584 A | 8/1999 | Ardito et al. | |
| 6,050,970 A | 4/2000 | Baerveldt | |
| 6,077,299 A | 6/2000 | Adelberg et al. | |
| 6,168,575 B1 | 1/2001 | Soltanpour | |
| 6,186,974 B1 | 2/2001 | Allan et al. | |
| 6,261,256 B1 | 7/2001 | Ahmed | |
| 6,450,984 B1 | 9/2002 | Lynch et al. | |
| 6,508,779 B1 | 1/2003 | Suson | |
| 6,544,208 B2 | 4/2003 | Ethier et al. | |
| 6,589,198 B1 | 7/2003 | Soltanpour et al. | |
| 6,726,664 B2 | 4/2004 | Yaron et al. | |
| 6,885,895 B1 | 4/2005 | Whitehurst et al. | |
| 7,006,870 B1 | 2/2006 | Whitehurst et al. | |
| 7,093,818 B2 | 8/2006 | Koeneman | |
| 7,854,600 B2 | 12/2010 | Ogawa | |
| 9,101,445 B2 | 8/2015 | Bigler et al. | |
| 9,655,779 B2 | 5/2017 | Bigler et al. | |
| 10,596,035 B2 | 3/2020 | Stergiopulos et al. | |
| 10,603,214 B2 | 3/2020 | Bigler et al. | |
| 2002/0087111 A1 | 7/2002 | Ethier et al. | |
| 2004/0162545 A1 | 8/2004 | Brown et al. | |
| 2005/0053501 A1 | 3/2005 | Akahori | |
| 2005/0256447 A1 | 11/2005 | Richardson et al. | |
| 2006/0175357 A1* | 8/2006 | Hammond | B65D 83/663 222/394 |
| 2007/0154336 A1 | 7/2007 | Miyazaki et al. | |
| 2009/0099626 A1 | 4/2009 | De Juan, Jr. et al. | |
| 2009/0208350 A1 | 8/2009 | Miyazaki et al. | |
| 2010/0114006 A1* | 5/2010 | Baerveldt | A61M 27/002 604/8 |
| 2011/0066098 A1 | 3/2011 | Stergiopulos | |
| 2013/0123684 A1 | 5/2013 | Giuffrida et al. | |
| 2013/0150775 A1* | 6/2013 | Dos Santos | A61F 9/00781 604/9 |
| 2013/0211312 A1 | 8/2013 | Gelvin | |
| 2014/0277266 A1 | 9/2014 | Khalil et al. | |
| 2014/0304773 A1 | 10/2014 | Woods et al. | |
| 2017/0348149 A1 | 12/2017 | Stergiopulos et al. | |
| 2017/0348151 A1* | 12/2017 | Ahmed | A61F 9/00781 |
| 2020/0214891 A1 | 7/2020 | Bigler et al. | |

FOREIGN PATENT DOCUMENTS

| | | |
|---|---|---|
| JP | S547791 A | 1/1979 |
| JP | H06509732 A | 11/1994 |
| JP | H10503405 A | 3/1998 |
| JP | 2004340184 A | 12/2004 |
| WO | WO-9112037 A1 | 8/1991 |
| WO | WO-9303778 A1 | 3/1993 |
| WO | WO-9603944 A1 | 2/1996 |
| WO | WO-9962586 A1 | 12/1999 |
| WO | WO-9966862 A1 | 12/1999 |
| WO | WO-0194784 A1 | 12/2001 |
| WO | WO-2009066133 A1 | 5/2009 |
| WO | WO-2011114260 A1 | 9/2011 |
| WO | WO-2014036437 A1 | 3/2014 |
| WO | WO-2018009556 A1 | 1/2018 |
| WO | WO-2020049508 A1 | 3/2020 |

OTHER PUBLICATIONS

International Search Report & Written Opinion dated Mar. 29, 2012 in Int'l PCT Patent Application No. PCT/EP2012/050455.
International Search Report & Written Opinion dated Feb. 20, 2020 in Int'l PCT Patent Application No. PCT/IB2019/057509.
Johnstone, et al., Aqueous Veins and Open Angle Glaucoma, The Glaucoma Book: A Practical, Evidence-Based Approach to Patient Care, Chapter 7:65-78 (2010).
Kiel, Jeffrey W., Ocular Perfusion Pressure, IOP and the Ocular Starling Resistor Effect, The Ocular Circulation Dec. 31, 2010 (pp. 13-16).
Sponsel, et al., Retrobulbar Diversion of Aqueous Humor: Clinical Feasibility Studies, J. Glaucoma, 23(9):628-632 (2014).
International Search Report & Written Opinion dated May 17, 2021 in Int'l PCT Patent Appl. Serial No. PCT/IB2021/051698.

* cited by examiner

APPARATUS FOR TREATING EXCESS INTRAOCULAR FLUID HAVING AN ELASTIC MEMBRANE

CROSS-REFERENCE TO RELATED APPLICATIONS

This application claims the benefit of priority of U.S. Provisional Application No. 62/986,604, filed Mar. 6, 2020, the entire contents of which are incorporated herein by reference. This application is also related to PCT International Application No. PCT/IB2019/057509, filed Sep. 6, 2019, published as WO 2020/049508 A1 on Mar. 12, 2020, which claims the benefit of priority of U.S. Provisional Application No. 62/728,022, filed Sep. 6, 2019, the entire contents of each of which are incorporated herein by reference. This application is further related to U.S. patent application Ser. No. 15/612,988, filed Jun. 2, 2017, now U.S. Pat. No. 10,596,035, which claims the benefit of priority of U.S. Provisional Application No. 62/346,456, filed Jun. 6, 2016, the entire contents of each of which are incorporated herein by reference.

FIELD OF INVENTION

This application relates to an apparatus for draining excess intraocular fluid to relieve intraocular pressure, for example, for treating glaucoma.

BACKGROUND OF THE INVENTION

Glaucoma affects about 70 million people worldwide, and is a disorder associated with high pressure in the eye resulting from the generation of excess intraocular fluid (aqueous humor). Aqueous humor is produced at a rate of 2-3 µl/min by the ciliary body and in a normal human eye maintains a constant intraocular pressure ("IOP") around 12-20 mmHg. Aqueous humor exits the eye primarily through the trabecular meshwork and Schlemm's canal, where it eventually drains to the episcleral veins. Maintaining intraocular pressure within appropriate ranges is critical to health of the eye, and depends on aqueous humor dynamics, namely the production rate from the ciliary body (aqueous humor inflow) and its outflow rate through the trabeculum. The most frequent type of glaucoma, called open-angle glaucoma, results from an increase in the fluidic resistance of the trabecular meshwork. Left untreated, this disease typically causes damage to the optic nerve, with consequent loss of vision, initially peripheral, but progressively leading to total blindness. Unfortunately, glaucoma is often asymptomatic until late in the progress of the disease.

Traditionally, glaucoma is treated using medication, for example, the daily application of eye drops, such as Brinzolamide ophthalmic, that reduce production of aqueous humor. Such medications do not cure glaucoma, and must be continue to be taken to maintain intraocular pressures within accepted limits. In certain cases, such treatment may fail and other surgical treatments are employed, such as filter procedures or placement of a glaucoma drainage device. Glaucoma drainage devices reduce intraocular fluid pressure by providing an artificial drainage pathway, thus maintaining a low TOP.

Previously-known glaucoma drainage devices usually comprise a structure having a drainage tube that is inserted through a small incision made in the conjunctiva. The surgeon makes a tiny incision in the sclera of the eye and creates an opening for the drainage implant device. The drainage tube is placed such that the opening of the tube is disposed in the anterior chamber of the eye within the aqueous humor. The tube is sutured in place with the drainage device attached to the sclera of the eye. Many surgeons will place an absorbable suture around the tube at the time of surgery to prevent over-filtration through the device until a fibrous capsule has formed. Accordingly, such devices typically are not functional until about 3 to 8 weeks after the procedure, so as to prevent over-filtration.

An exemplary previously-known passive glaucoma drainage device is described in U.S. Pat. No. 4,457,757 to Molteno. The device described in that patent comprises a tube of a biologically inert silicone configured to be inserted into the eye to drain aqueous humor from the anterior chamber of the eye. The device does not include a pressure regulating mechanism, but instead relies on the resistance to aqueous flow through the tubing to prevent over drainage.

One drawback of devices such as those described in the Molteno patent is that the drainage flow depends on IOP and on the fixed hydrodynamic resistance of the shunt. In many cases, however, the hydrodynamic resistance of the shunt may not be sufficient to reduce high IOP when the resistance to flow is too high, or may lead to over-drainage if the resistance is low. For example, a common problem, which arises shortly after implantation, is hypotony, which occurs when IOP drops below acceptable physiological levels (i.e., IOP<6 mmHg). Hypotony usually takes place the first few days to weeks following the implantation of a glaucoma drainage device, and is a combined result of a low fluidic resistance of both the implant and the distal outflow paths. Hypotony may lead to a number of undesirable effects and complications, such as hypotensive maculopathy, cataract formation and optic nerve edema. Another problem, also related to the fixed fluid resistance of previously known implants, is fibrosis, which appears progressively at long term and which, depending on its extent and severity, may raise the effective fluidic resistance of the implant, thereby raising the IOP to different, often non-physiological, levels.

The foregoing drawbacks have been recognized in the prior art, and several improvements have been attempted to improve flow control over the entirely passive system described in Molteno.

For example, U.S. Pat. No. 5,411,473 to Ahmed describes a drainage device that includes a membrane-type valve. More specifically, Ahmed describes a drainage system including a membrane folded and held in tension between two plates to provide a slit opening, such that the membrane responds to pressure changes to open or close the slit opening. Unfortunately, the operational characteristics of the system depend on the properties of the membrane, which cannot be changed easily once the device is implanted. Also, the valve of Ahmed does not provide a true opening pressure to accurately control post-operation IOP.

U.S. Pat. No. 6,544,208 to Ethier describes a self-regulating pressure system. More specifically, Ethier describes an implantable shunt device having a flexible tube positioned in a pressurized enclosure. In this patent, flow through the tube is dependent on a differential pressure between a pressure in the flexible tube and a pressure outside the flexible tube in the pressurized enclosure. However, one skilled and experienced in the field of medical implants, especially in ophthalmology, would understand that such a system with a constant external pressure chamber would be very impractical, if not impossible, to make.

Ethier further describes that the pressure outside the flexible tube in the pressurized enclosure of the implantable shunt device is generated by osmotic effects. More specifically, the pressurized enclosure is filled with a solution containing a solute that generates an osmotic pressure which controls the opening pressure of the implantable shunt device. The implantable shunt device includes a semipermeable membrane affixed between support gratings that reduce deformation of the semi-permeable membrane. Unfortunately, significant deformation of the semi-permeable membrane makes it difficult to predict the osmotic pressure within the pressurized enclosure.

U.S. Pat. No. 9,101,445 to Bigler describes an ocular drainage system for treating diseases that produce elevated intraocular pressures, such as glaucoma, wherein the system includes an implantable device and an external control unit. The implantable device includes a non-invasively adjustable valve featuring at least one deformable tube and a disk rotatably mounted within a housing, such that rotation of the disk using the external control unit causes the disk to apply a selected amount of compression to the deformable tube, thereby adjusting the fluidic resistance of the deformable tube and regulating the intraocular pressure.

Still other examples of previously-known systems are known. U.S. Pat. Nos. 5,626,558 and 6,508,779 to Suson describe a shunt which may be adjusted after implantation by using a low power laser to drill additional openings in the tube wall to adjust the flow rate. U.S. Pat. No. 6,186,974 to Allan et al. describes a drainage shunt having multiple layers, one of which may be a gel that swells upon absorption of fluid to adjust flow rate through the tube. U.S. Pat. No. 6,726,664 to Yaron describes a drainage tube including a distal hook that retains the distal end of the implant within the anterior chamber of the eye, and various means, such as rods or sutures, for partially occluding the lumen of the tube to regulate flow.

Other previously-known glaucoma treatment systems include significantly greater complexity to address the drawbacks of the simpler shunt systems described above. For example, U.S. Pat. No. 6,077,299 to Adelberg, et al. describes a non-invasively adjustable valve implant for the drainage of aqueous humor for treatment of glaucoma, wherein an implant having an inlet tube is surgically inserted in the anterior chamber of the eye to allow aqueous humor to flow from the anterior chamber to a valve. After passing through a pressure and/or flow regulating valve in the implant, the fluid is dispersed along the periphery of the implant to the interior of the Tenon's capsule where it is absorbed by the body. In one embodiment, the valve inhibits flow below, and allows flow above, a specific pressure difference between the IOP within the eye and the pressure within the bleb cavity in the Tenon's capsule. The specified pressure difference or set-point is always positive and the valve is always closed in the presence of negative pressure differences, to prevent reverse flow of fluid from the Tenon's capsule back into the anterior chamber of the eye.

In Adelberg, the valve is formed by a chamber to which the inlet tube is connected, such that the chamber is closed by a pressure sensitive valve in the shape of a flat cone. The pressure regulation set point of the valve is governed by a flexible diaphragm that cooperates with an armature plate having an inclined surface, and which is configured to slide over a complementary inclined surface attached to the diaphragm. Cooperation of the inclined surface of the plate and the complementary surface causes the diaphragm to deflect depending on where the armature plate is located. The armature plate is rotated, using a rotor and a set of speed-reducing and torque-enhancing gears, to regulate the flow through the device. The characteristics of the valve strongly depend on the configuration of the cone shaped valve. In addition, the regulating mechanism is complex, including many rotating parts and gears, and this complexity poses a risk of malfunction.

In view of the drawbacks of the foregoing prior art devices and methods, it would be desirable to provide an ocular drainage system and methods that are capable of maintaining a constant, or nearly constant, TOP.

It further would be desirable to provide an ocular drainage system effective to prevent hypotony post-implantation and/or effective in light of the development of fibrosis at long term.

It further would be desirable to provide an ocular drainage system having few moving parts, thereby enhancing robustness of the system and reducing the risk of failure arising from operation of complex mechanisms.

It further would be desirable to provide an ocular drainage system having a small volume to facilitate implantation of the device beneath the conjunctiva, either under a relatively small scleral flap or on the scleral surface, or even within a diffuser plate.

Finally, it would be desirable to provide an ocular drainage system wherein moving parts of the system are configured to reduce the risk of clogging or seizing due to the buildup of proteinaceous sediments.

SUMMARY

The present invention overcomes the drawbacks of previously-known ocular drainage systems by providing an implantable device for the treatment of excess fluid pressure within an eye as described herein. The device includes a housing shell sized and shaped to be implanted beneath the conjunctiva, e.g., under a scleral flap. The housing shell has a first end sized and shaped for fluid communication with an anterior chamber of the eye, a second end sized and shaped for fluid communication with a space beneath tissue of the eye, e.g., a space beneath the conjunctiva or a rear space of the eye such as an orbital fat space of the eye, and defining a cavity between the first end and the second end. Accordingly, the second end of the housing shell permits drainage into the space beneath the conjunctiva or the rear space of the eye.

The device further includes an elastic membrane disposed within the cavity to divide the cavity into a fluidic channel that permits a flow of fluid from the first end to the second end and a sealed cavity. The elastic membrane is constructed to deform to change the volume of the fluidic channel, and accordingly, the volume of the sealed cavity, responsive to pressure fluctuations between the first and second ends, thereby varying the fluidic resistance of the flow of fluid through the fluidic channel. The elasticity of the elastic membrane is selected to establish a balance between an external pressure at the second end and an internal pressure of the eye at the first end. In accordance with one aspect of the present invention, the fluidic channel has a rectangular-shaped cross-section.

The housing shell may have a radius of curvature selected to accommodate a radius of curvature of the eye, and may be formed of a biocompatible material. The outer surface of the housing shell may have a cylindrical shape. In accordance with one aspect of the present invention, the housing shell is sized and shaped to be implanted above a sclera. Accordingly, a protective patch may be positioned above the housing shell to protect a conjunctival layer from device-induced erosion.

Further, the first end of the housing shell includes an inlet connector, and the second end of the housing shell includes an outlet connector. The device further may include a nozzle having an outlet end coupled to the inlet connector, and an inlet end sized and shaped to pass through a wall of the eye to communicate with the anterior chamber of the eye. In addition, the device may include a draining tube having a proximal end coupled to the outlet connector, and a distal region sized and shaped to be disposed within the space beneath the tissue of the eye. For example, the distal region of the drainage tube may include one or more drainage holes. Accordingly, the space may be an orbital fat space such that the one or more drainage holes permit drainage into the orbital fat space.

In accordance with another aspect of the present invention, the device includes a diffuser plate, e.g., a Seton tube, sized and shaped to be disposed beneath the tissue of the eye, wherein the diffuser plate has a groove sized and shaped to receive a portion of the distal region of the drainage tube. Alternatively, the diffuser plate may be directly coupled to the outlet connector of the implantable device, e.g., the housing shell may be disposed within the diffuser plate.

The device also may preferably include a local constriction disposed within a portion of the cavity of the housing shell to reduce the area in the cavity that forms the fluidic channel to increase fluidic resistance of the flow of fluid through the fluidic channel, e.g., adjacent the local constriction. Accordingly, the local constriction forms a lower surface of the fluidic channel, and the elastic membrane forms an upper surface of the fluidic channel.

In accordance with another aspect of the present invention, the cavity has a circular-shaped cross-section. For example, the local constriction may be positioned along a central longitudinal axis of the cavity. In this embodiment, the elastic membrane is positioned around the local constriction, thereby forming the fluidic channel circumferentially around the local constriction. In accordance with yet another aspect of the present invention, the local constriction may have one or more grooves disposed along its outer surface, such that the one or more grooves define the fluidic channel.

In accordance with yet another aspect of the present invention, the local construction is structured such that it causes the flow of fluid to flow from the first end having first flow area, through the fluidic channel having a second flow area smaller than the first flow area, and exit through the second end having a third flow area greater than the second flow area. For example, the elastic member may include a tube, such that the local constriction is disposed within the tube and coupled to at least a portion of an inner surface of the tube, thereby defining the fluidic channel between a remaining portion of the inner surface of the tube and the local constriction. Moreover, the local constriction may include one or more indentations disposed at either or both ends of the local constriction. The one or more indentations are structured to assist in disposing the local constriction within the tube.

BRIEF DESCRIPTION OF THE DRAWINGS

The above features and advantages of the present invention will be apparent upon consideration of the following detailed description, taken in conjunction with the accompanying drawings, in which like reference characters refer to like parts throughout, and in which.

DETAILED DESCRIPTION

In accordance with the principles of the present invention, an implantable device is provided for treating excessive intraocular pressure within an eye. In a preferred embodiment, the implantable device includes a cavity and an elastic membrane disposed within the cavity, thereby creating a fluidic passageway through the device. The elastic membrane is self-regulating to control the flow of aqueous humor from an anterior chamber of the eye, through the passageway, to a sink outside the eye (e.g., a bleb formed under a scleral flap or the orbital fat space of the eye). In accordance with one aspect of the present invention, the implantable device includes an area of local constriction disposed within the cavity to reduce the area of the fluidic passageway to increase fluidic resistance of the flow of fluid through the passageway. In an alternative embodiment, the implantable device includes a circular-shaped passageway such that the elastic membrane is positioned around the local constriction along the longitudinal axis of the passageway. The elastic membrane has an elasticity that allows the implantable device to maintain intraocular pressures within a desired range, thereby reducing the risk of damage to the optic nerve without requiring re-operation.

The device of the present invention is expected to provide a number of advantages over the previously-known devices and methods, including:

self-regulating pressure within the device to adapt to pressure changes either in the interior chamber of the eye, or distally at the output;

limiting the increase of IOP as a result of an increase of downstream pressure due to development of fibrosis;

limiting the decrease of IOP to avoid hypotony, especially during the time period shortly following implantation of the implantable device; and/or a low volume design that facilitates implantation under a relatively small scleral flap or simply on the scleral surface, or even within a diffuser plate.

Figure 1A:
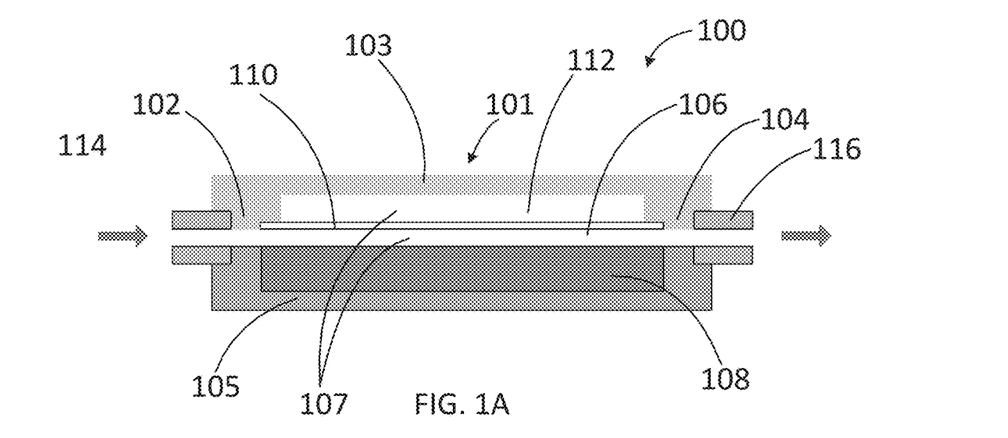
FIG. 1A is a schematic diagram illustrating the geometry of an exemplary device for the treatment of excess fluid pressure within an eye in accordance with the principles of the present invention.
Figure 1B:
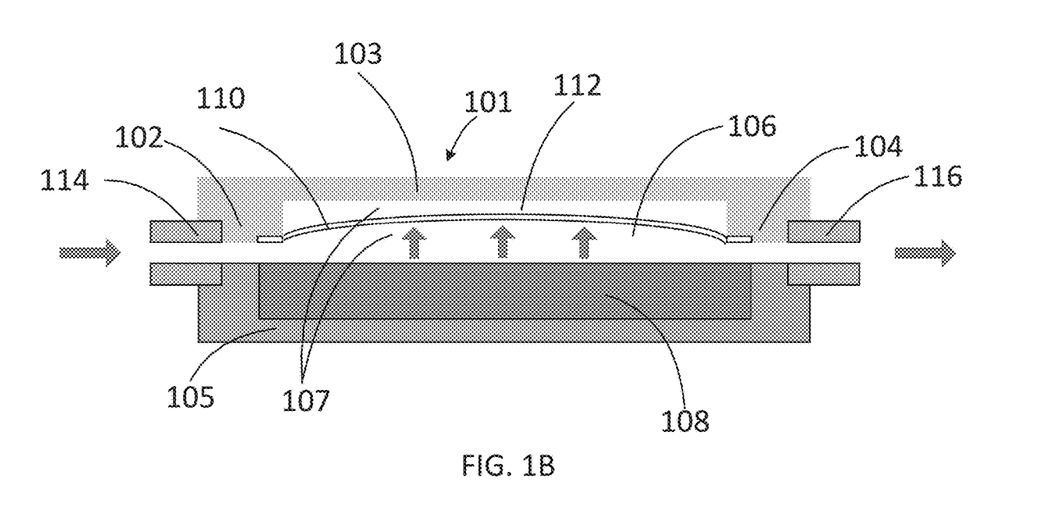
FIG. 1B is a schematic diagram illustrating the device of FIG. 1A in response to a pressure differential between the inlet and outlet ends of the device.

Referring now to FIGS. 1A and 1B, an exemplary device for the treatment of excess intraocular pressure within an eye is described. Implantable device 100 includes housing shell 101 having upper portion 103, lower portion 105, inlet end 102 and outlet end 104. Housing shell 101 preferably has a cylindrically-shaped outer surface, and may be made from a biocompatible, waterproof or water-resistant plastic such as polyether ether ketone ("PEEK"), polycarbonate or titanium. The use of PEEK or similar polymer is particularly desirable, as such polymers provide good biocompatibility and long-term structural stability when implanted. Upper portion 103 and lower portion 105 may be separate pieces and molded together during manufacturing of device 100, or alternatively, upper portion 103 and lower portion 105 may be formed as a single piece.

Implantable device 100 is configured to be implanted within the eye, e.g., under the conjunctiva, which may be formed using techniques as commonly known in the field of glaucoma filtration surgery. The human eye is generally spherical, having a radius of curvature of approximately 11 mm. While implantable device 100 may be fabricated as a cylindrical device, advantageously housing shell 101 may include a concave recess on the exterior of lower portion 105 and convex shape on the exterior of upper portion 103, each having a curvature that approximates that of the human eye so that implantable device 100 will lie snugly against the exterior of the eye beneath a scleral flap. Preferably, the radius of curvature R of lower portion 105 of housing shell 101 is in a range of about 10 mm to about 12 mm, and more preferably about 11 mm.

In addition, housing shell 101 has cavity 107 there, which may extend through housing shell 101 to permit fluid flow from inlet end 102 to outlet end 104. Cavity 107 may have a circular cross-section within housing shell 101. In accordance within another aspect of the present invention, cavity 107 may have a rectangular cross-section within housing shell 101. As shown in FIGS. 1A and 1B, device 100 includes elastic membrane 110 disposed within cavity 107 having a first end coupled to inlet end 102 and a second end coupled to outlet end 104, thereby dividing cavity 107 into sealed cavity 112 between an inner surface of upper portion 103 of housing 101, and fluidic channel 106 between elastic membrane 110 and lower portion 105 of housing 101. Sealed cavity 112 may be filled with a compressible gas, e.g., air, and may be leak-proof. Elastic membrane 110 preferably is constructed of a flexible biocompatible material that requires a predetermined level of force to deform within sealed cavity 112 to thereby change the volume of fluidic channel 106, and accordingly the volume of sealed cavity 112, responsive to pressure fluctuations across inlet end 102 and outlet end 104.

Local constriction 108 may be positioned within cavity 107 adjacent lower portion 105 of housing 100, thereby reducing the area in cavity 107 that forms fluidic channel 106 to increase fluidic resistance of the flow of fluid through fluidic channel 106. As will be understood by a person ordinarily skilled in the art, local constriction 108 and lower portion 105 of housing shell 101 may be separate pieces and molded together during manufacturing of device 100, or alternatively, local constriction 108 and lower portion 105 may be formed as a single piece.

As illustrated in FIGS. 1A and 1B, cavity 107 of housing shell 101 may have an inlet passageway adjacent inlet end 102 and an outlet passageway adjacent outlet end 104, both having a height and/or width consistent with that of fluidic channel 106 formed by local constriction 108 and/or elastic membrane 110. Advantageously, aqueous humor drained from the eye flows only through the interior of fluidic channel 106, while elastic membrane 110 separates fluidic channel 106 from sealed cavity 112. Sealed cavity 112 is leak-proof which ensures that fluid such as, e.g., aqueous humor, or proteinaceous materials contained within the aqueous humor, traveling through fluidic channel 106 does not enter sealed cavity 112, and thus will not fill, clog or block sealed cavity 112, thereby reducing the risk of component failure.

Device 100 also includes inlet connector 114 coupled to inlet end 102, such that inlet connector 114 is in fluid communication with fluidic channel 106, and outlet connector 116 coupled to outlet end 104, such that outlet connector 116 is in fluid communication with fluidic channel 106. Inlet connector 114 and outlet connector 116 allows device 100 to be coupled to additional drainage tubes such that fluid passing from inlet end 102 to outlet end 104 may be deposited with a bleb formed in the sclera of the patient's eye. For example, aqueous humor from the anterior chamber of the eye enters device 100 via inlet connector 114, passes through fluidic channel 106 and outlet connector 116 to the exterior of the eye, typically inside a cavity formed by the scleral flap cavity. In accordance with the principles of the present invention, the rate of drainage, and consequently, the IOP, depends on the fluidic resistance of fluidic channel 106 based on the elasticity of elastic membrane 110.

FIG. 1A depicts expected operation of implantable device 100 at regular IOP levels, e.g., when the downstream external pressure is very low (<3 mmHg). As illustrated in FIG. 1A, elastic membrane 110 and local constriction 108 define fluidic channel 106 within cavity 107 of housing shell 101 having a flow area and a corresponding fluidic resistance when elastic membrane 110 is in its undeformed state. In this case, the balance of forces between the pressure applied against elastic membrane 110 from within sealed cavity 112 and the pressure forces within fluidic channel 106 as a result of the flow of aqueous humor from the anterior chamber of the eye from inlet end 102, through fluidic channel 106, and to a sink outside the eye via outlet end 104, define the geometry of elastic membrane 110, the cross-sectional area of fluidic channel 106, and therefore its hydraulic resistance. In this case, implantable device 100 will maintain a near-constant desired IOP at physiological levels at inlet end 102 even if flow or pressure at outlet end 104 changes.

Fluid flow from inlet end 102 to outlet end 104 within fluidic channel 106 applies pressure to the interior surface of elastic membrane 110. If the internal pressure within fluidic channel 106 increases beyond a predetermined amount, elastic membrane 110 will "bulge" out, e.g., deform into sealed cavity 112 as shown in FIG. 1B, thereby decreasing the hydraulic resistance of fluidic channel 106.

Here, a simple viscous resistance law is applied:

$$\frac{P_{in} - P_{out}}{R} = Q; \text{ therefore, } P_{in} = P_{out} + R*Q$$

As downstream external pressure ($P_{out}$) increases, the pressure within fluidic channel 106 will initially increase as it is always bounded between upstream intraocular pressure ($P_{in}$) at inlet end 102 to downstream external pressure ($P_{out}$) at outlet end 104. Thus, elastic membrane 110 will "bulge" into sealed cavity 112. This will increase the cross-sectional area and overall volume of fluidic channel 106, and thus lower hydraulic resistance (R) to a level such that $P_{in}$ will be effectively unchanged.

FIG. 1B illustrates expected operation of implantable device 100 when there is, for example, an increase in IOP levels at inlet end 18. For example, if flow increases, IOP will increase and the average pressure forces within fluidic channel 106 will increase, which will cause elastic membrane 110 to bulge, e.g., deform into sealed cavity 112, resulting in a larger flow area, smaller fluidic resistance and consequently a decrease in IOP, thereby allowing the IOP to be maintained at a pre-determined desired level. Any scenario causing IOP to increase will result in deformable structure equilibrating at a new, larger flow area and increased flow that will result in turn reduce IOP. As illustrated in FIG. 1B, the expansion of elastic membrane 110 has a parabolic shape along elastic membrane 101, such that fluidic channel 106 has the largest cross-sectional area adjacent the center of elastic membrane 110, and reduces in size toward inlet end 102 and outlet end 104 where elastic membrane 110 is fixed to housing shell 101.

Similarly, if pressure at outlet end 104 increases, for example, due to the development of fibrosis at outlet end 20, the average pressure within fluidic channel 106 will increase, causing elastic membrane 110 to deform into sealed cavity 112, which in turn will result in increased flow area and smaller fluidic resistance within fluidic channel 106. Consequently, the increase of IOP at inlet end 102 will be limited.

In accordance with one aspect of the present invention, if IOP at inlet end 102 decreases, for example, during the period of time right after implantation which may cause hypotony, the average pressure within fluidic channel 106 will decrease, which may cause elastic membrane 110 to deform toward fluidic channel 106, thereby increasing the volume of sealed cavity 112 and resulting in a smaller flow area and larger fluidic resistance within fluidic channel 106. This in turn will limit the decrease of IOP at inlet end 102 and reduce the risk of hypotony.

Figure 2:
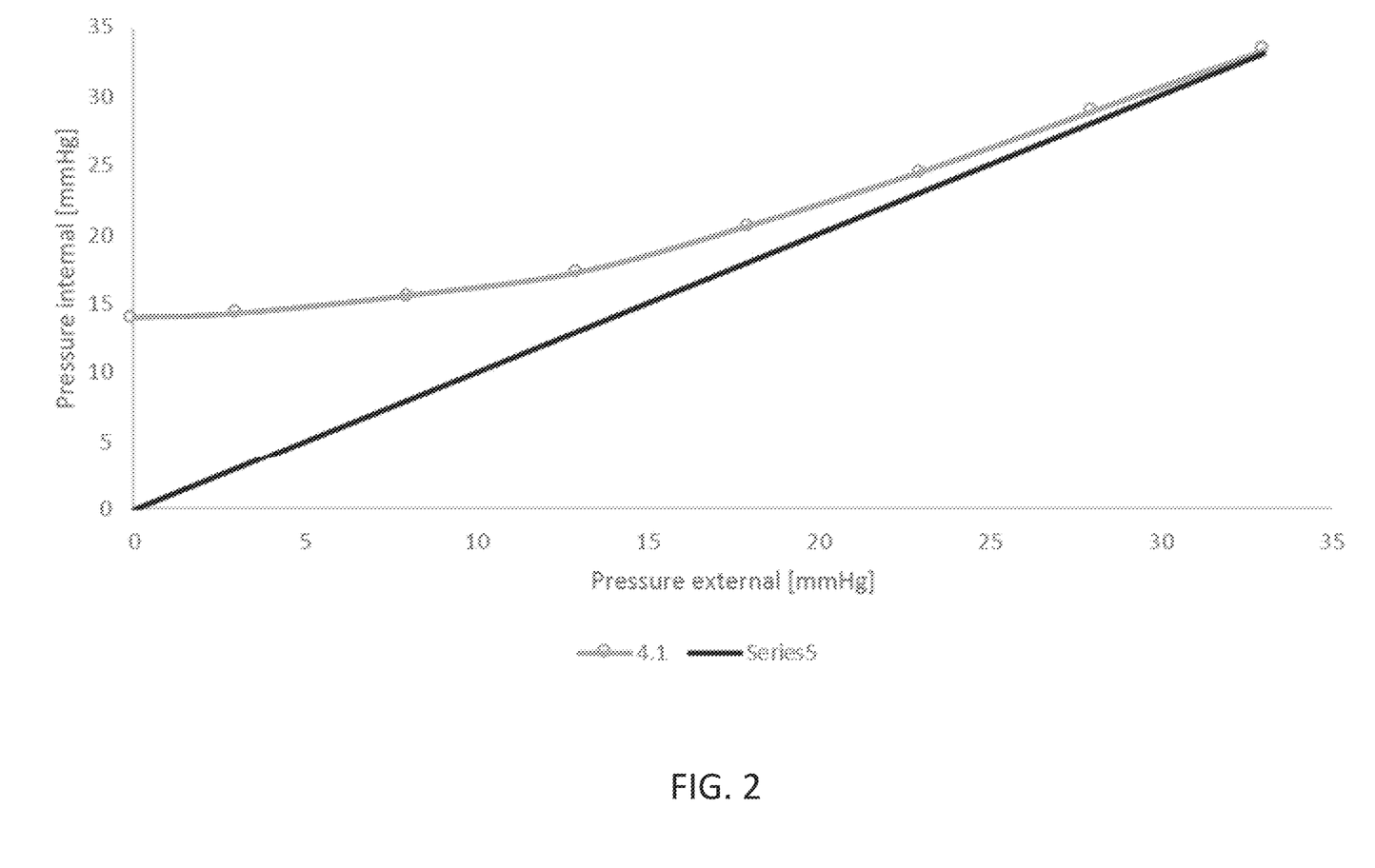
FIG. 2 is graph showing upstream pressure (IOP) vs. downstream pressure of an exemplary device for the treatment of excess fluid pressure within an eye constructed in accordance with the principles of the present invention.

For a given flow through fluidic channel 106, device 100 becomes an upstream pressure regulator in the sense that, if fluidic pressure within fluidic channel 106 increases, elastic membrane 110 will deform into sealed cavity 112 and the hydraulic resistance will decrease. In this case, the pressure at inlet end 102 is maintained relatively constant as illustrated in FIG. 2. FIG. 2 is a graph depicting upstream pressure at the inlet end of the device, i.e., internal intraocular pressure within the eye, versus downstream pressure at the outlet end of the device, external pressure, from an vitro test on a 1:1 scale prototype of device 100. As shown in FIG. 2, when downstream pressure varies from 0 to 15 mmHg, upstream pressure is maintained relatively constant, e.g., around 15 mmHg.

Figure 3A:
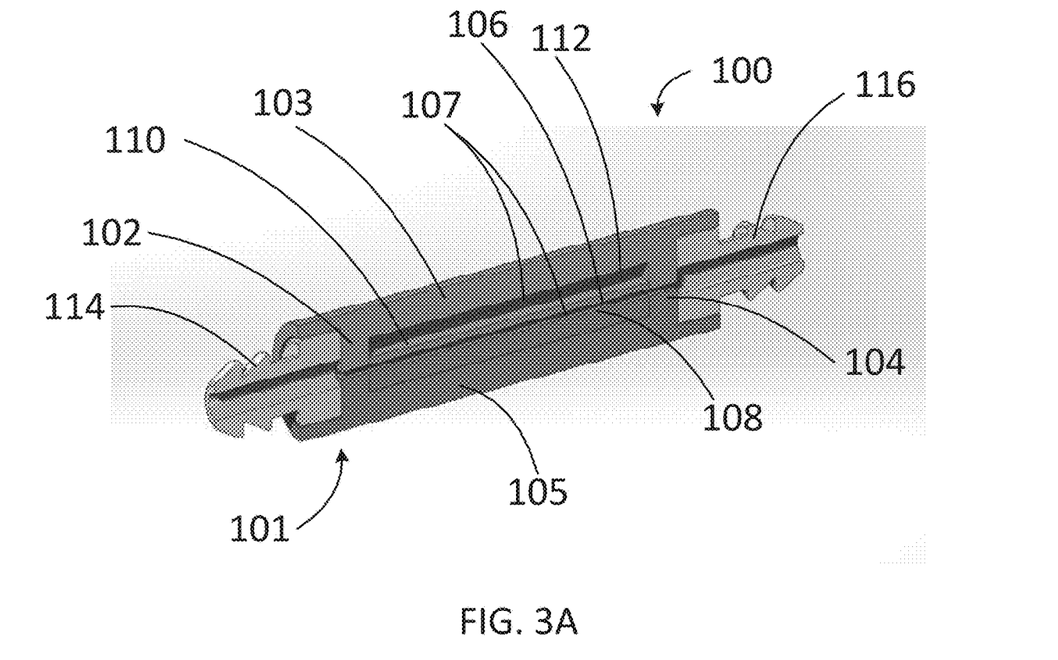
FIG. 3A is a side sectional view of an exemplary device for the treatment of excess fluid pressure within an eye constructed in accordance with the principles of the present invention.
Figure 3B:
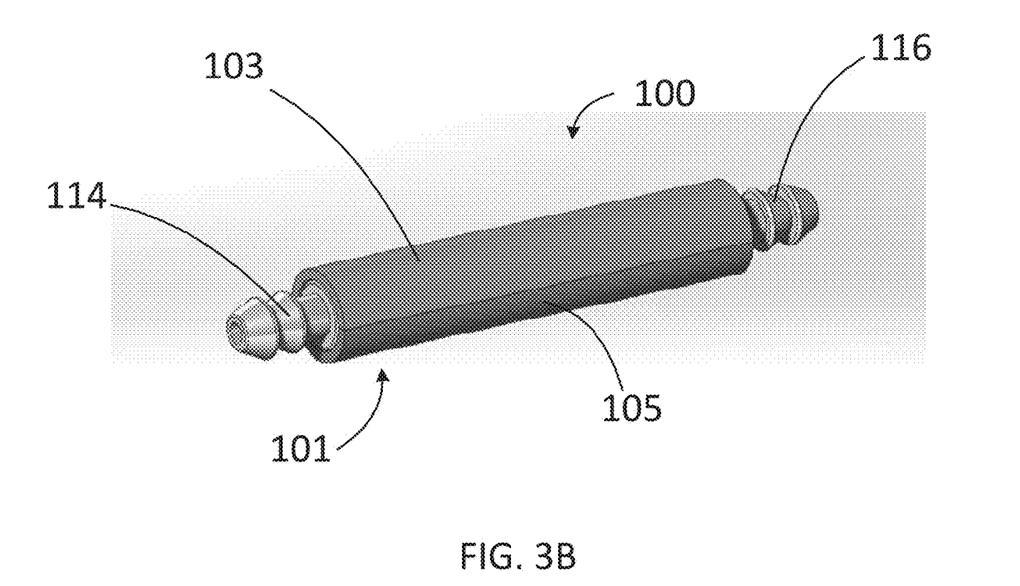
FIG. 3B is a perspective view of the exemplary device of FIG. 3A.

Referring now to FIGS. 3A and 3B, an exemplary embodiment of the device for the treatment of excess fluid pressure within an eye constructed in accordance with the principles of the present invention is described. As shown in FIGS. 3A and 3B, housing 101 has a cylindrically-shaped outer surface. Inlet connector 114 and outlet connector 116 are sized and shaped to be coupled with additional drainage tubes such that fluidic channel 106 may be in fluidic communication with the anterior chamber of the eye as well as a space, e.g., orbital fat space, of the eye. For example, the outer surface of inlet connector 114 and outlet connector 116 may have ridges for a fluid-tight connection with the additional drainage tubes such that external bodily fluids may not enter the lumen of inlet connector 114 and outlet connector 116, and consequently fluidic channel 106. As illustrated in FIG. 3A, the lumens of inlet connector 114 and outlet connector 116 may have a circular cross-sectional area. Aqueous humor enters fluidic channel 106 via the lumen of inlet connector 114 and a narrow passageway at inlet end 102, and exits device 100 via a narrow passageway at outlet end 104 and the lumen of outlet connector 116.

Figure 4A:
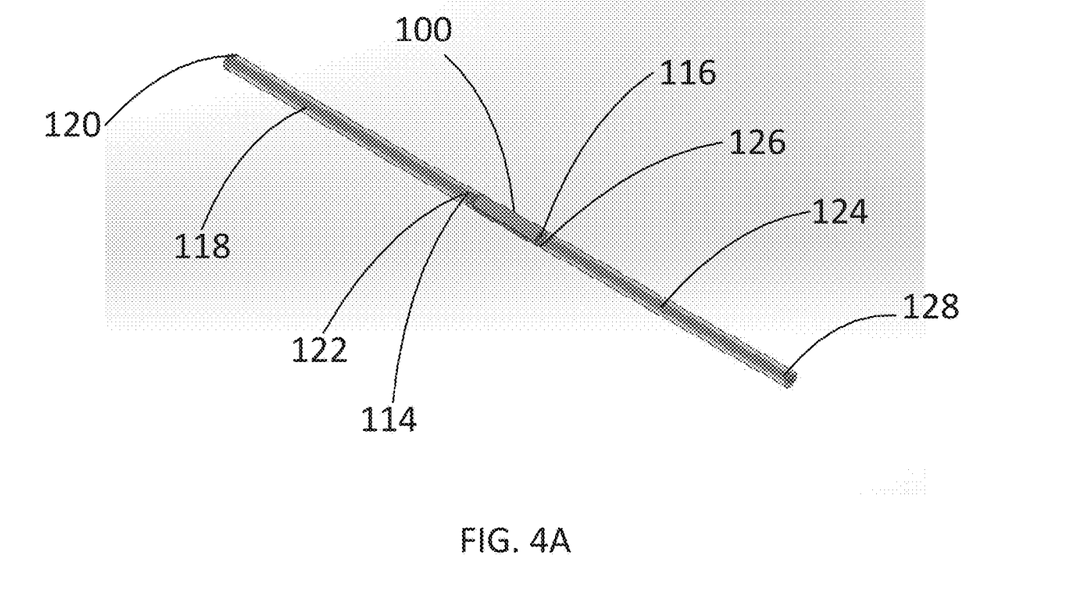
FIG. 4A illustrates the exemplary device of FIG. 3A coupled to a nozzle and a drainage tube in accordance with the principles of the present invention.
Figure 4B:
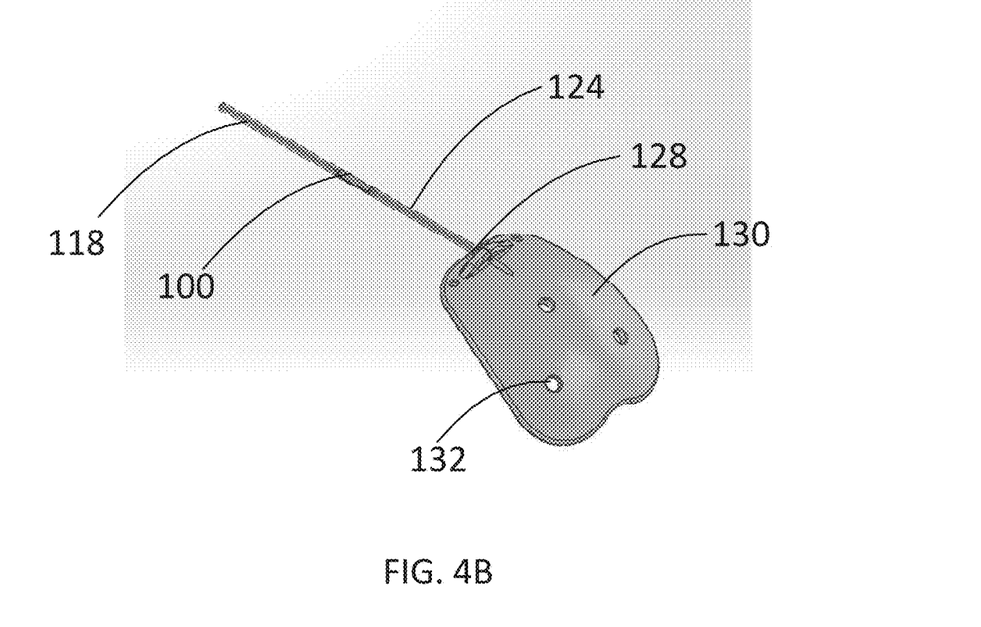
FIG. 4B illustrates the exemplary device of FIG. 3A coupled to a nozzle and a diffuser plate via a drainage tube in accordance with the principles of the present invention.

Referring now to FIGS. 4A and 4B, device 100 may be coupled to various drainage tubes for treatment of excess fluid pressure within a patient's eye. For example, as illustrated in FIG. 4A, device 100 may be coupled to nozzle 118 via inlet connector 114. Nozzle 118 has proximal end 120, distal end 122, and a lumen extending therebetween sized and shaped for flow of aqueous humor from proximal end 120 to distal end 122. Distal end 122 may be removably coupled to inlet connector 114 of implantable device 100, e.g., after implantation of nozzle 118 and after implantation of implantable device 100. Nozzle 118 is designed to extend from inlet connector 114 and be disposed through the wall of the eye and into the anterior chamber. For example, proximal end 120 of nozzle 118 is sized and shaped to extend through the wall of the eye and into the anterior chamber when device 100 is implanted beneath a flap formed in a patient's sclera. To facilitate the introduction of nozzle 118 into the anterior chamber of the eye, proximal end 120 of nozzle 118 may have a conical or sharpened extremity that facilitates piercing of the scleral tissue and introduction of the nozzle into the anterior chamber. Distal end 122 is sized and shaped to receive inlet connector 114 of device 100 in a fluid-tight manner such that external bodily fluids cannot enter housing shell 101. Accordingly, the lumen of nozzle 118 is in fluid communication with fluidic channel 106 of device 100 via the lumen of inlet connector 114.

In addition, device 100 may be coupled to drainage tube 124. Drainage tube 124 has proximal end 126, distal region 128, and a lumen extending therebetween sized and shaped for flow of aqueous humor from proximal end 126 to distal end 128. Proximal end 126 may be removably coupled to outlet connector 116 of implantable device 100, e.g., after implantation of drainage tube 124 and after implantation of implantable device 100. Drainage tube 124 preferably has a length such that it extends from outlet connector 116 and distal region 128 is disposed within a space beneath tissue of the eye, e.g., a space beneath the conjunctiva or an orbital fat space of the eye, for drainage of aqueous humor therein. Distal region 128 may include one or more drainage holes such that the lumen of drainage tube 128 may be in fluid communication with the orbital fat space of the eye. Drainage tube 128 may be made of, for example, silicone, and may be sufficiently flexible to accommodate the curvature of the patient's eye.

Flow exiting through drainage tube 128 is deposited within the sclera, where it drains primarily to the connecting vein network. Alternatively, a surgeon may make a second scleral flap with a large cavity beneath it (a bleb) and then form a channel to connect the scleral cavity holding the implantable device to the second cavity. In this case, aqueous humor exiting drainage tube 128 will flow via the channel to the second cavity, where it will be absorbed. Alternatively, flow exiting through drainage tube 128 drains directly to the suprachoroidal space between the sclera and the choroid of the eye.

Referring now to FIG. 4B, device 100 may be coupled to nozzle 118 via inlet connector 114 as described above, and further coupled to diffuser plate 130, e.g., a Seton tube, via outlet connector 116 and drainage tube 124. For example, distal region 128 of drainage tube 124 may be coupled to diffuser plate 130. Flow exiting through outlet connector 116 travels through drainage tube 124 into diffuser plate 130 and is ultimately deposited within the sclera, where it drains primarily to the connecting vein network. Specifically, drainage tube 124 coupled to diffuser plate 130 may be positioned so that diffuser plate 130 is disposed on the surface of the eye such that aqueous humor may be absorbed into the scleral tissue, e.g., into the connecting vein network, and distal region 128 of drainage tube 124 is disposed in a space, e.g., the orbital fat space, of the eye, such that aqueous humor may be absorbed into the orbital fat space of the eye. Diffuser plate 130 may be curved to accommodate the curvature of the eye and may include eyelets 132 shaped and sized to permit diffuser plate 130 to be implanted and remain in position once implanted on an exterior surface of the eye via, e.g., sutures. In this embodiment, diffuser plate 130 may include one or more drainage holes along its upper surface such that the lumen of drainage tube 124 may be in communication with the upper surface of diffuser plate 130.

Diffuser plate 130 may be positioned along drainage tube 125 in between proximal end 126 and the one or more drainage holes disposed along distal region 128 of drainage tube 124. For example, diffuser plate 130 may include a groove shaped and sized to receive drainage tube 124, and drainage tube 124 may be maintained within the groove via, e.g., friction or an adhesive. In this embodiment, the one or more drainage holes along distal end 128 of drainage tube 124 in proximity to the groove allows aqueous humor within the lumen of drainage tube 124 to be in communication with the upper surface of diffuser plate 130. Accordingly, when proximal end 126 of drainage tube 124 is coupled to outlet connecter 116 of implantable device 100, aqueous humor that exits outlet connecter 116 of implantable device 100 may exit via the one or more drainage holes and drain over the upper surface of diffuser plate 130 into the scleral tissue, and/or exit via the one or more drainage holes at distal region 128 of drainage tube 124 into the orbital fat space. In this case, overall resistance of aqueous humor through drainage tube 124, e.g., due to tissue growth at either the one or more drainage holes, may be maintained within a desired limit.

In accordance with another aspect of the present invention, implantable device 100 is designed to be implanted within the diffuser plate on the scleral surface of a human eye. In this embodiment, the nozzle is sized and shaped to extend from within the diffuser plate along the curvature of the eye and to be disposed through the wall of the eye and into the anterior chamber. Flow enters the implantable device through the nozzle coupled to the inlet connector of the device and exits through the outlet connector into the diffuser plate and is ultimately deposited beneath the tissue of the eye, where it drains primarily to the connecting vein network.

In accordance with one aspect of the present invention, implantable device 100 may be implanted beneath the conjunctiva, on the scleral surface of the eye. In this embodiment, a protective patch, e.g., a layer of allograft tissue, may be positioned above the implantable device to protect the adjacent conjunctival layer from device-induced erosion.

Figure 5A:
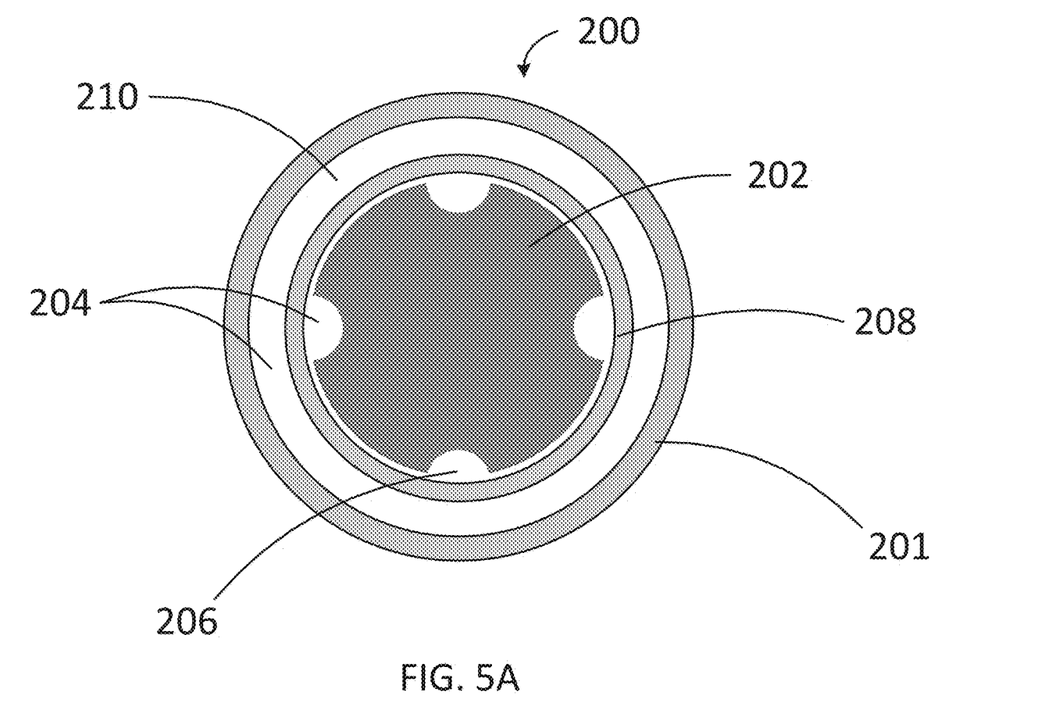
FIG. 5A is a cross-sectional view of another exemplary device for the treatment of excess fluid pressure within an eye in accordance with the principles of the present invention.
Figure 5B:
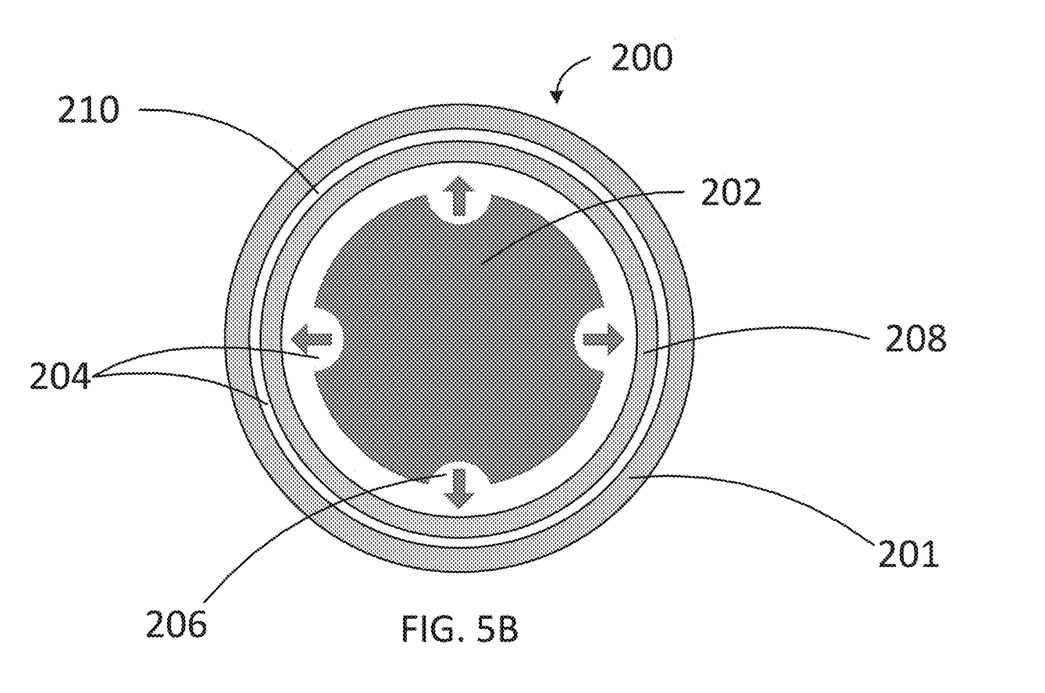
FIG. 5B is a cross-sectional view illustrating the device of FIG. 5A in response to a pressure differential between the inlet and outlet ends of the device.

Referring now to FIGS. 5A and 5B, an alternative exemplary embodiment of the device for the treatment of excess fluid pressure within an eye constructed in accordance with the principles of the present invention is described. Device 200 is based on the same principles as device 100 described above, such that increased pressure within the fluidic channel of device 200 causes an elastic membrane to "bulge," thereby enlarging the flow area and reducing hydraulic resistance within the fluidic channel. Housing shell 201 has a cylindrical-shaped outer surface, and inlet end and an outlet end, and defining cavity 204 between the inlet end and the outlet end. Device 200 differs from device 100 in that local constriction 202 has a circular cross-section and is positioned along the longitudinal axis of cavity 204 of cylindrical-shaped housing shell 201. As shown in FIGS. 5A and 5B, local constriction 202 includes one or more grooves along its outer surface, thereby creating one or more respective fluidic channels 206. As will be understood by a person having ordinary skill in the art, local constriction 202 may have fewer or more than four grooves, and accordingly, device 200 may have few or more than four fluidic channels.

Aqueous humor flows from the inlet end of device 200, through the one or more fluidic channels 206, and out the outlet end of device 200. In addition, device 200 includes elastic membrane 208 positioned circumferentially around local constriction 202 within cavity 204, thereby dividing cavity 204 into sealed cavity 210 between an inner surface of housing shell 201 and elastic membrane 208, and one or more fluidic channels 206 between the grooves of local constriction 202 and elastic membrane 208. Elastic membrane 208 is fixed at one end to the inlet end of device 200, and at the opposite end to the outlet end of device 200. Therefore, as pressure within one or more fluidic channels 206 increase, elastic membrane 208 "bulges" toward sealed cavity 210 in the direction of the arrows as shown in FIG. 5B, which causes the flow area of the one or more fluidic channels 206 to increase, thereby decreasing hydraulic resistance through one or more fluidic channels 206.

Figure 6A:
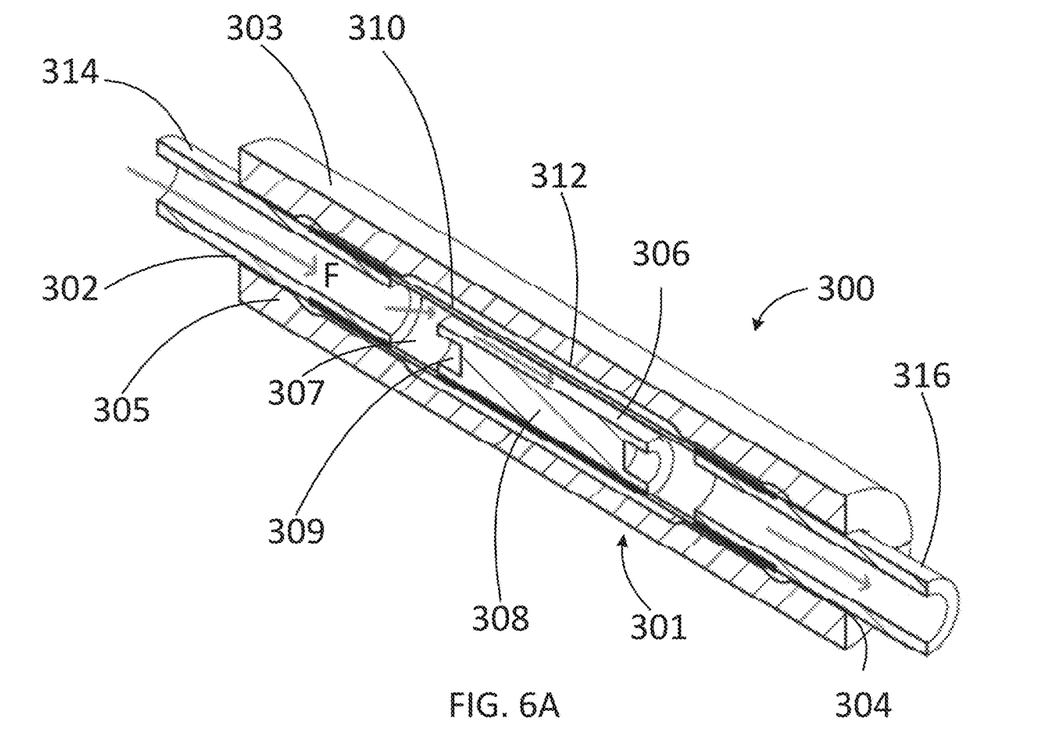
FIG. 6A is a side sectional view of an alternative exemplary device for the treatment of excess fluid pressure within an eye constructed in accordance with the principles of the present invention.
Figure 6B:
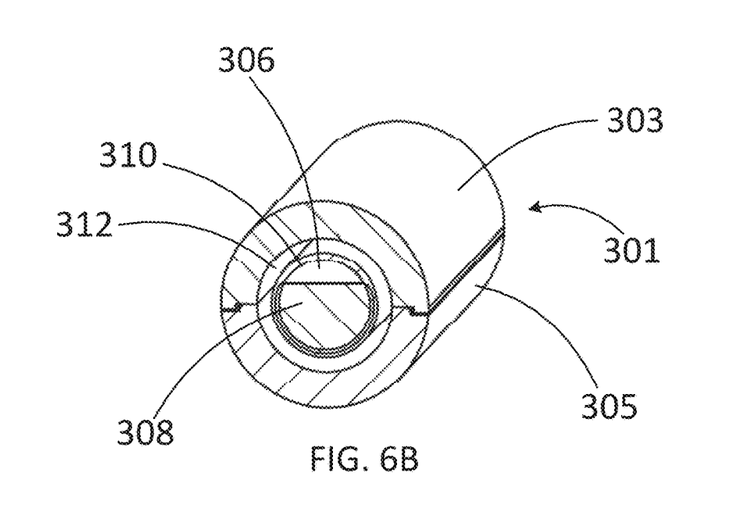
FIG. 6B is a cross-sectional view of the device of FIG. 6A.

Referring now to FIGS. 6A and 6B, another exemplary device for the treatment of excess intraocular pressure within an eye is described. Implantable device 300 includes housing shell 301 having upper portion 303, lower portion 305, inlet end 302 and outlet end 304. Housing shell 301 preferably has a cylindrically-shaped outer surface, and like housing shell 101 of FIG. 3A, may be made from a biocompatible, waterproof or water-resistant plastic such as polyether ether ketone ("PEEK"), polycarbonate or titanium. Upper portion 303 and lower portion 305 may be separate pieces and molded together during manufacturing of device 300, or alternatively, upper portion 303 and lower portion 305 may be formed as a single piece.

Implantable device 300 is configured to be implanted within the eye, e.g., under the conjunctiva. While implantable device 300 may be fabricated as a cylindrical device, advantageously housing shell 301 may include a concave recess on the exterior of lower portion 305 and convex shape on the exterior of upper portion 303, each having a curvature that approximates that of the human eye so that implantable device 300 will lie snugly against the exterior of the eye beneath a scleral flap.

In addition, housing shell 301 has a lumen which may extend through housing shell 301 to permit fluid flow from inlet end 302 to outlet end 304. As shown in FIG. 6A, at least a portion of the lumen of housing shell 301 may have a larger cross-sectional area than the portions of the lumen adjacent inlet end 302 and outlet end 304, thereby forming cavity 307 between inlet end 302 and outlet end 304. Cavity 107 may have a circular cross-section within housing shell 301. As shown in FIGS. 6A and 6B, device 300 includes tubular elastic membrane 310 disposed within cavity 307 having a first end coupled to the inner surface of the lumen of housing shell 301 adjacent inlet end 302 and a second end coupled to the inner surface of the lumen of housing shell 301 adjacent outlet end 304, thereby dividing cavity 307 into sealed cavity 312 between an inner surface of housing 301 and the outer surface of elastic membrane 310, and fluidic channel 306 in fluid communication with inlet end 302 and outlet end 304. Like sealed cavity 112 of FIG. 3A, sealed cavity 312 may be filled with a compressible gas, e.g., air, and may be leak-proof. Elastic membrane 310 preferably is constructed of a flexible biocompatible material that requires a predetermined level of force to deform within sealed cavity 312, thereby changing the volume of fluidic channel 306, and accordingly the volume of sealed cavity 212, responsive to pressure fluctuations across inlet end 302 and outlet end 304.

Local constriction 308 may be positioned within tubular elastic membrane 310 within cavity 307. For example, as shown in FIG. 6B, local constriction 308 may be disposed within elastic membrane 310 such that a portion of the outer surface of local constriction 308, e.g., half or more than half of the outer surface of local construction 308, is directly coupled to a portion of the inner surface of elastic membrane 310. Accordingly, the portion of the inner surface of elastic membrane 310 and the portion of the outer surface of local constriction 308 that are not coupled define fluidic channel 106, thereby reducing the area of fluidic channel 306 to increase fluidic resistance of the flow of fluid through fluidic channel 306. Referring again to FIG. 6A, local constriction 308 may be suspended within cavity 307 via elastic membrane 310. Thus, elastic membrane 310 has sufficient rigidity to maintain local constriction 308 within cavity 307 without deforming into sealed cavity 312 adjacent lower portion 305 of housing shell 301 due to the weight of local constriction 308. As shown in FIG. 6A, local constriction 308 may optional one or more indentations 309 on either or both ends of local constriction 308 to assist with assembly of local constriction 308 within tubular elastic membrane 310. For example, indentations 309 may be cylindrical indentations cut out from local constriction 108. As will be understood by a person having ordinary skill in the art, indentations 309 may have other cross-sectional shapes other than a circle including, but not limited to, a square or triangle.

As illustrated in FIG. 6A, device 300 also may include inlet connector 314 coupled to inlet end 302, such that inlet connector 314 is in fluid communication with fluidic channel 106, and outlet connector 316 coupled to outlet end 304, such that outlet connector 316 is in fluid communication with fluidic channel 306. For example, inlet connector 314 and outlet connector 316 may have an outer diameter that is substantially the same size as the lumen of housing shell 301 such that inlet connector 314 and outlet connector 316 is snugly positioned within inlet end 302 and outlet end 304, respectively. Moreover, the lumens of inlet connector 314 and outlet connector 316 may have a size substantially similar, or slightly less than, the lumen of elastic membrane 310. Accordingly, aqueous humor drained from the eye flows into device 300 via the lumen of inlet connector 314 in the direction of arrow F, then through fluidic channel 106 defined by elastic membrane 310 and local constriction 308 having a smaller flow area and thus higher fluidic resistance, and exits via the lumen of outlet connector 316 having a larger flow area. Advantageously, the aqueous humor flows only through the interior of fluidic channel 306, while elastic membrane 310 separates fluidic channel 306 from leak-proof, sealed cavity 312.

Like inlet connector 114 and outlet connector 116, inlet connector 314 and outlet connector 316 allows device 300 to be coupled to additional drainage tubes such that fluid passing from inlet end 302 to outlet end 304 may be deposited with a bleb formed in the sclera of the patient's eye, as described in further detail below.

As illustrated in FIG. 6A, elastic membrane 310 and local constriction 308 define fluidic channel 306 within cavity 307 of housing shell 301 having a flow area and a corresponding fluidic resistance when elastic membrane 310 is in its undeformed state. In this case, the balance of forces between the pressure applied against elastic membrane 310 from within sealed cavity 312 and the pressure forces within fluidic channel 306 as a result of the flow of aqueous humor from the anterior chamber of the eye from inlet end 302, through fluidic channel 306, and to a sink outside the eye via outlet end 304, define the geometry of elastic membrane 310, the cross-sectional area of fluidic channel 306, and therefore its hydraulic resistance. In this case, implantable device 300 will maintain a near-constant desired IOP at physiological levels at inlet end 302 even if flow or pressure at outlet end 304 changes.

Fluid flow from inlet end 302 to outlet end 304 within fluidic channel 306 applies pressure to the interior surface of elastic membrane 310. If the internal pressure within fluidic channel 306 increases beyond a predetermined amount, elastic membrane 310 will "bulge" out, e.g., deform into sealed cavity 312, thereby decreasing the hydraulic resistance of fluidic channel 306. As downstream external pressure increases, the pressure within fluidic channel 306 will initially increase as it is always bounded between upstream intraocular pressure at inlet end 302 to downstream external pressure at outlet end 304. Thus, elastic membrane 310 will "bulge" into sealed cavity 312. This will increase the cross-sectional area and overall volume of fluidic channel 306, and thus lower hydraulic resistance to a level such that upstream intraocular pressure at inlet end 302 will be effectively unchanged.

Moreover, like device 100 of FIG. 1A, device 300 may be coupled to various drainage tubes for treatment of excess fluid pressure within a patient's eye. For example, device 300 may be coupled to nozzle 118 of FIG. 4A via inlet connector 314. Distal end 122 of nozzle 118 may be removably coupled to inlet connector 314 of implantable device 300, e.g., after implantation of nozzle 118 and after implantation of implantable device 300. In addition, device 300 may be coupled to drainage tube 124 of FIG. 4A. Proximal end 126 of drainage tube 124 may be removably coupled to outlet connector 316 of implantable device 300, e.g., after implantation of drainage tube 124 and after implantation of implantable device 300. Further, device 300 may be coupled to nozzle 118 via inlet connector 314 as described above, and further coupled to diffuser plate 130, e.g., a Seton tube, via outlet connector 316 and drainage tube 124.

In accordance with another aspect of the present invention, implantable device 300 may be designed to be implanted within the diffuser plate on the scleral surface of a human eye. Flow enters device 300 through the nozzle coupled to inlet connector 314 of device 300 and exits through outlet connector 316 into the diffuser plate and is ultimately deposited beneath the tissue of the eye, where it drains primarily to the connecting vein network. In accordance with one aspect of the present invention, implantable device 300 may be implanted beneath the conjunctiva, on the scleral surface of the eye. In this embodiment, a protective patch, e.g., a layer of allograft tissue, may be positioned above the implantable device to protect the adjacent conjunctival layer from device-induced erosion.

Methods of implanting and using an implantable device constructed in accordance with the principles of the present invention are now provided. An implantable device (e.g., device 100, 200, or 300) may be implanted using a surgical technique similar to that used for prior art glaucoma drainage devices. As will be understood, for the exemplary devices described herein constructed in accordance with the principles of the present invention, a scleral flap is created in a manner analogous to standard trabeculectomy, and the flap is dissected carefully up to clear cornea. The scleral flap is lifted and care is taken to identify the center of the "blue zone" adjacent to clear cornea, which corresponds to the location of the trabecular meshwork. As will be understood by one of skill in the art, the "blue zone" generally is located posterior to the anterior limbal border, and terminates in midlimbal line. A 26-gauge needle is inserted into the anterior chamber through the center of the "blue zone" at an angle parallel to the plane of the iris. Next, the nozzle of the implantable device is inserted into the anterior chamber through the ostium created by the needle until the housing lies flush against the eye. The scleral flap then is sutured in place, e.g., using a 10-0 nylon suture with a spatulated needle. Finally the conjunctiva is carefully sutured closed to complete the implantation process.

Alternatively, a small incision is made in the conjunctiva as an opening for the implantable device. The implantable device is positioned on the sclera surface such that the opening of the nozzle is disposed through a wall of the eye in the anterior chamber of the eye, within the aqueous humor. The implantable device then may be connected to a Seton tube coupled to a diffuser plate above the sclera of the eye, a drainage tube, or a drainage tube coupled to a diffuser plate above the sclera of the eye. Optionally, a layer of allograft tissue may be sutured in place over the implantable device to reduce the risk of erosion of the adjacent conjunctival layer. Finally the conjunctiva is carefully sutured closed to complete the implantation process.

Alternative embodiments of the ocular drainage system of the present invention may include a miniaturized pressure sensor disposed with the implantable device and in communication with the inlet conduit to measure TOP. This sensor may be coupled to a miniaturized telemetry system, such as those based on radio frequency identification principles that may be energized from a distance, to emit a signal that can be received and interpreted by an external receiver. This arrangement would provide a ready way in which to non-invasively determine TOP.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A device for the treatment of excess fluid pressure within an eye, the device comprising:
   a housing shell configured to be implanted beneath a conjunctiva, the housing shell having a first end configured for fluid communication with an anterior chamber of the eye, a second end configured for fluid communication with a space beneath tissue of the eye, and defining a cavity between the first end and the second end;
   an elastic membrane comprising a tube disposed within the cavity to divide the cavity into a sealed cavity and a fluidic channel that permits a flow of fluid from the first end to the second end; and
   a local constriction disposed within the tube and coupled to at least a portion of an inner surface of the tube, thereby defining the fluidic channel between a remaining portion of the inner surface of the tube and the local constriction, the local constriction configured to increase a fluidic resistance of the flow of fluid through the fluidic channel adjacent the local constriction,
   wherein the elastic membrane is configured to deform to change a volume of the fluidic channel responsive to pressure fluctuations between the first and second ends, thereby varying the fluidic resistance of the flow of fluid through the fluidic channel.

2. The device of claim 1, wherein the housing shell has a radius of curvature selected to accommodate a radius of curvature of the eye.

3. The device of claim 1, wherein the housing shell is configured to be implanted under a scleral flap.

4. The device of claim 1, wherein an outer surface of the housing shell comprises a cylindrical shape.

5. The device of claim 1, wherein the housing shell is configured to be implanted above a sclera, the device further comprising a protective patch configured to protect a conjunctival layer from device-induced erosion, wherein the protective patch is positioned above the housing shell.

6. The device of claim 1, wherein the first end of the housing shell comprises an inlet connector, and the second end of the housing shell comprises an outlet connector.

7. The device of claim 6, further comprising a nozzle having an outlet end coupled to the inlet connector, and an inlet end configured to pass through a wall of the eye to communicate with the anterior chamber of the eye.

8. The device of claim 6, further comprising a drainage tube having a proximal end coupled to the outlet connector, and a distal region configured to be disposed within the space beneath the tissue of the eye.

9. The device of claim 8, wherein the distal region of the drainage tube comprises one or more drainage holes.

10. The device of claim 8, further comprising a diffuser plate having a groove configured to receive a portion of the distal region of the drainage tube, the diffuser plate configured to be disposed beneath the tissue of the eye.

11. The device of claim 10, wherein the diffuser plate is a Seton tube.

12. The device of claim 6, further comprising a diffuser plate coupled to the outlet connector, the diffuser plate configured to be disposed beneath the tissue of the eye.

13. The device of claim 12, wherein the housing shell is disposed within the diffuser plate.

14. The device of claim 1, wherein the second end is configured for fluid communication with a space beneath the conjunctiva or a rear space of the eye such as an orbital fat space, such that the second end of the housing shell permits drainage into the space beneath the conjunctiva or the rear space of the eye.

15. The device of claim 1, wherein the local constriction forms a lower surface of the fluidic channel, and wherein the elastic membrane forms an upper surface of the fluidic channel.

16. The device of claim 1, wherein the cavity has a circular-shaped cross-section, wherein the local constriction is positioned along a central longitudinal axis of the cavity, and wherein the elastic membrane is positioned around the local constriction, thereby forming the fluidic channel circumferentially around the local constriction.

17. The device of claim 16, wherein the local constriction comprises one or more grooves disposed along an outer surface of the local constriction, the one or more grooves defining the fluidic channel.

18. The device of claim 1, wherein the local constriction causes the flow of fluid to flow from the first end having first flow area, through the fluidic channel having a second flow area smaller than the first flow area, and exit through the second end having a third flow area greater than the second flow area.

19. The device of claim 1, wherein a lower surface of the local constriction is coupled to the at least a portion of the inner surface of the tube along an entire length of the local constriction, such that an upper surface of the local constriction and the remaining portion of the inner surface of the tube that are not coupled define the fluidic channel extending along the entire length of the local constriction.

20. The device of claim 19, wherein the local constriction comprises one or more indentations disposed at either or both ends of the local constriction, the one or more indentations configured to assist in disposing the local constriction within the tube.

21. The device of claim 1, wherein an elasticity of the elastic membrane is selected to establish a balance between an external pressure at the second end and an internal pressure of the eye at the first end.

\* \* \* \* \*